United States Patent [19]

Caspari et al.

[11] Patent Number: 4,549,540
[45] Date of Patent: Oct. 29, 1985

[54] THIGH RESTRAINING APPARATUS AND METHOD

[75] Inventors: Richard B. Caspari, Maidens; Terry L. Whipple; James A. Thimsen, both of Richmond, all of Va.

[73] Assignee: Precision Surgical Instruments, Inc., Richmond, Va.

[21] Appl. No.: 552,375

[22] Filed: Nov. 16, 1983

[51] Int. Cl.$^4$ ............................................. A61F 13/00
[52] U.S. Cl. .................................................... 128/133
[58] Field of Search ................ 128/133, 132, 327, 653

[56] References Cited

U.S. PATENT DOCUMENTS

| | | | |
|---|---|---|---|
| 4,232,681 | 11/1980 | Tulaszewski | 128/653 |
| 4,243,039 | 1/1981 | Aginsky | 128/327 |
| 4,299,213 | 11/1981 | Violet | 128/133 |
| 4,457,302 | 7/1984 | Caspari et al. | 128/133 |
| 4,466,437 | 7/1984 | Dyck | 128/327 |

Primary Examiner—C. Fred Rosenbaum
Assistant Examiner—Christa K. Scott
Attorney, Agent, or Firm—Richard P. Matthews

[57] ABSTRACT

A thigh restraining apparatus especially useful in connection with arthroscopic knee surgery wherein the surgeon may perform the operation while viewing the knee on a television screen. A bar member extends across the operating table supported by horizontally extending rail members customarily provided on operating tables. A specially designed sphygmomanometer constitutes a tourniquet member and applies a known pressure to the thigh of the patient. A strap member envelops the thigh of the patient and is reeled out or in by a screw feed as required to accommodate the patient's thigh. One end of the strap is secured and an intermediate portion is removably attached to the sphygmomanometer. If necessary, both knees may be operated upon sequentially without disturbing a required sterile field by positioning a pair of strap feeding devices on opposite sides of the bar member and securing each strap to an adjacent sphygmomanometer applied to each of the patient's thighs.

10 Claims, 7 Drawing Figures

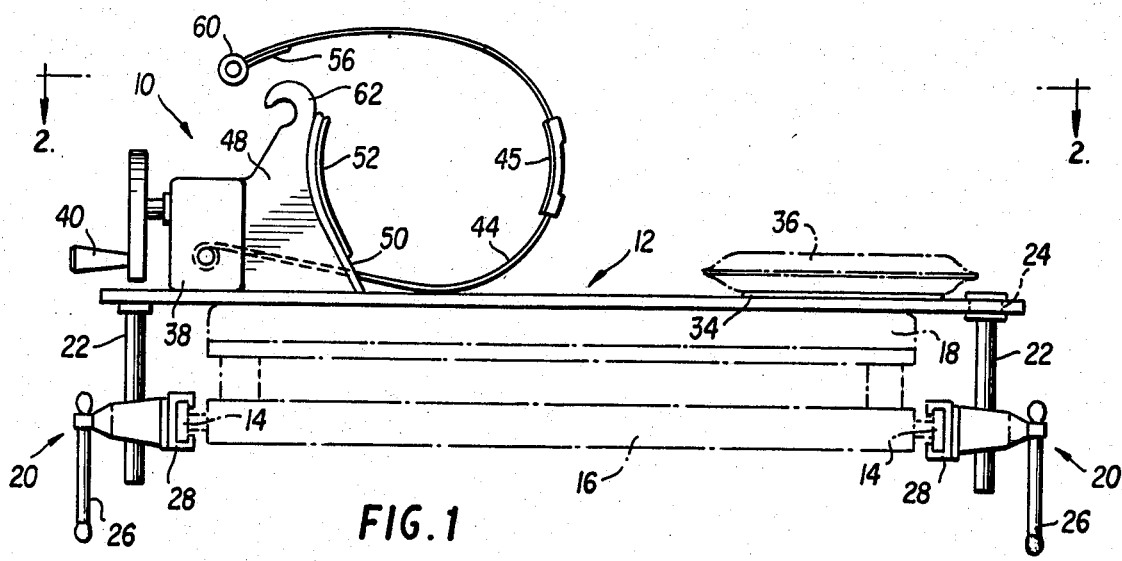
FIG. 1
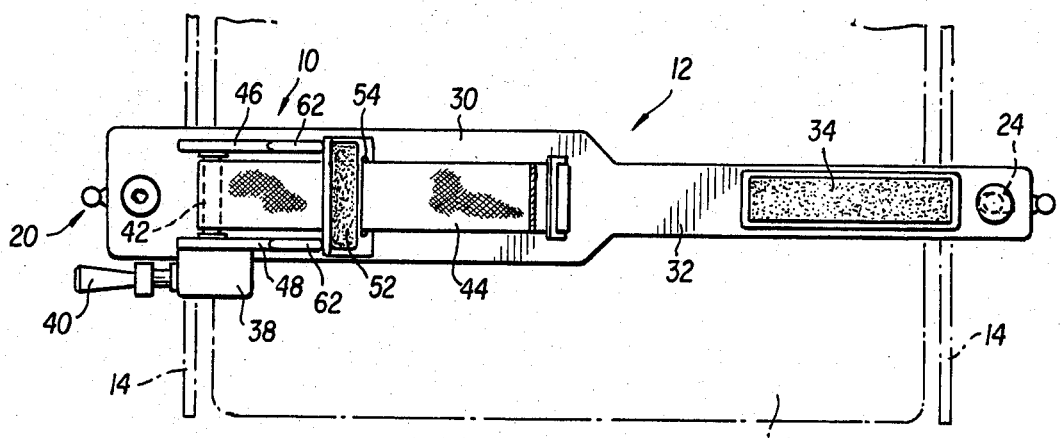
FIG. 2
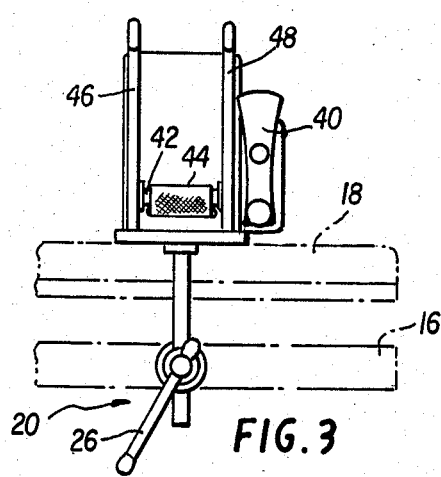
FIG. 3
FIG. 8

THIGH RESTRAINING APPARATUS AND METHOD

This invention relates to a leg immobilizing apparatus and, more particularly, to such an apparatus especially useful in connection with arthroscopic knee surgery.

BACKGROUND OF THE INVENTION

Arthroscopic surgery is being used much more frequently in knee surgery and in the diagnosis of knee injuries. An arthroscope resembles a long, very narrow tube and may be provided with a magnifying lens at one end. The arthroscope is inserted through a very small puncture wound of the knee, in the order of from 2–5 millimeters in diameter rather than a relatively large incision. The surgeon examines the knee through the arthroscope and inserts small instruments through other puncture sites. In the preferred arthroscope models used in the present invention the viewing area of the arthroscope is magnified and projected onto a television screen whereby the surgeon actually performs the surgery while viewing the television screen.

Because a substantially smaller puncture-type wound is made in the knee, the surgery may be performed under a local anesthetic and the operation may be completed in approximately twenty minutes as compared with from one and one half to two hours previously. Since the damage to the knee is so much less from the small puncture wounds, the patient's recovery time is substantially less. The patient customarily is up and walking within one day and in some instances even sooner.

It has been the practice in the past to use a post which did not permit any rotational control and a strap to hold the patient's leg immobile while the operation was being performed. Tourniquets were placed on the leg, but the amount of pressure applied has not been known. Moreover, it has been necessary to break the sterile field when other procedures, such as taking x-rays, operating on both knees, or the like, were required.

SUMMARY OF THE INVENTION

In accordance with the present invention the foregoing limitations and shortcomings of the known prior art are effectively overcome. In particular, the thigh restraining apparatus of the present invention provides a bar which extends completely across the operating table and is adjustably clamped to a pair of horizontally extending parallel rails customarily provided on operating tables. A tourniquet means in the form of a specially designed sphygmomanometer applies a known pressure to the thigh of the patient. This sphygmomanometer was originally disclosed in our copending patent application Ser. No. 439,439 filed Nov. 5, 1982, the disclosure of which is hereby incorporated by reference. A strap means is reeled out and in as required by a screw feed means mounted on the bar. The strap means envelops the thigh of the patient and is secured to the sphygomamanometer by means of Velcro pad means. Velcro is a trademark of Velcro, Inc., of Manchester, N.H., for separable fasteners, namely, hook and loop type fasteners. Specifically, one Velcro pad is carried by the strap means and engages a mating Velcro member on the sphygmomanometer on one side of the patient's thigh while a fixedly mounted Velcro pad engages a mating Velcro member on the sphygmomanometer located on the opposite side of the patient's thigh. The free end of the strap means is releasably retained so that the strap means under control of the reversible feed means snugly engages the sphygmomanometer around the patient's thigh.

An additional feature of the present invention makes it possible to operate sequentially on both of the patient's knees without disturbing or breaking the sterile field under which the operation is performed. Such a bilateral operation may be performed by mounting a bar member across the operating table and securing it to the rail members on opposite sides of the operating table in the same manner as when a single operation is to be performed. However, in this instance, a pair of the thigh restraining members are mounted on opposite ends of the bar member. A tourniquet member is applied to each of the patient's thighs and held by the thigh restraining members. After the sterile field is established over both of the patient's legs in a conventional manner, it is then possible to restrain one of the thigh's while knee surgery is performed on the restrained leg and then release that thigh and restrain the second thigh to operate on that knee without disturbing or breaking the sterile field.

The inherent advantages and improvements of the present invention will become more readily apparent upon reference to the following detailed description of the invention and by reference to the drawings wherein:

FIG. 1 is a front elevational view showing the thigh restraining apparatus of the present invention;

FIG. 2 is a top plan view taken in horizontal cross section along line 2—2 of FIG. 1;

FIG. 3 is a fragmentary end elevational view of the apparatus of FIG. 1;

FIG. 8 is a fragmentary front elevational view illustrating a modified form of the apparatus.

DETAILED DESCRIPTION OF THE INVENTION

Figure 4:
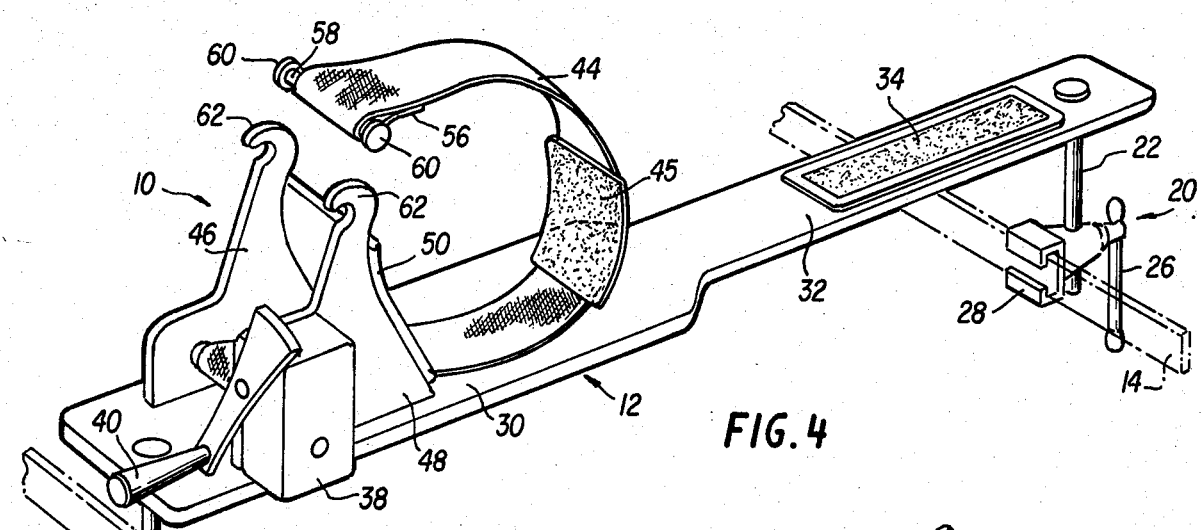
FIG. 4 is a perspective view of the apparatus of FIG. 1.

Referring now to FIG. 1 of the drawings, there is illustrated a thigh restraining apparatus indicated generally at 10. The thigh restraining apparatus 10 includes a bar means, designated generally at 12, which extends substantially entirely across the bed of an operating table which is provided with conventional and customary rail means which are indicated in phantom at 14. These rail means 14 are supported by a table or frame indicated in phantom at 16 with a cushion or mattress being shown at 18. Many operating tables have what has come to be known as a Clark clamp and one of these is indicated generally at 20. This Clark clamp constitutes clamping means and receives a pair of support pin members 22 at least one of which, such as the one on the right hand side of FIG. 1, is provided with a slot 24 so as to provide an adjustable width means for supporting the bar means 12. Although the details of the Clark clamp form no part of the instant invention, the clamp is shown to have a handle and a suitable rail gripping or engaging member 28.

As seen best in FIG. 2, the bar means 12 is provided with a relatively wide portion 30 and an intermediate necked in portion terminating in a narrow longitudinal portion 32. In this embodiment of the invention, the thigh restraining apparatus 10 is intended to restrain one thigh only and the bar means 12 may be turned end to end so as to accommodate the particular knee to be operated upon by restraining the associated thigh over the wide portion 30 of bar means 12. The narrow portion 32 is provided with a suitable retaining means 34, such as Velcro, to removably support a cushion or pillow 36 as shown in phantom in FIG. 1 in order to rest the thigh which is not being operated upon. Velcro is a trademark of Velcro, Inc., of Manchester, N.H. for separable fasteners, namely, hook and loop type fasteners.

The thigh restraining apparatus 10 mounted on the wide portion 30 of bar means 12 includes a suitable screw feed means received within housing 38. The screw feed means is turned in opposite directions by hand crank 40 which is preferably of a self-storing type. Thus, screw feed means are provided which includes a spool axis 42 which may be rotated in either direction so as to pay in or pay out strap means 44. In FIGS. 1, 4, 6 and 7 strap means 44 is shown to carry a Velcro pad 45 which is adjustable lengthwise along the strap means 44 until it is clamped against the thigh of a patient.

As seen in FIG. 3, mounting plate members 46, 48 are suitably attached to the bar means 12 and provided with a curved plate 50. This curved plate 50 carries another Velcro pad 52 which is intended to engage a tourniquet means 70 illustrated in detail in FIG. 5 and engaged in a manner to be described hereinafter. The curved plate 50 also includes a slot 54 through which the strap means 44 is paid out and in, and which serves to guide the strap means laterally in the course of feeding the strap means out and in. As seen in FIGS. 1 and 4, the strap means 44 is provided with an end portion 56 which is folded back and sewn to the strap after the end has been looped over a locking rod 58 which carries disc-like end retention members 60. The rod 58 is retained in open hook ends 62 in the mounting plate members 46, 48 making it possible to apply tension to the strap means 44. Thus, in the operation of the thigh restraining apparatus, once the locking rod 58 is received within the open hook ends 52, the hand crank 40 may be turned in the opposite direction to draw in and tension the strap as well as to tighten it against the thigh of the patient.

Figure 5:
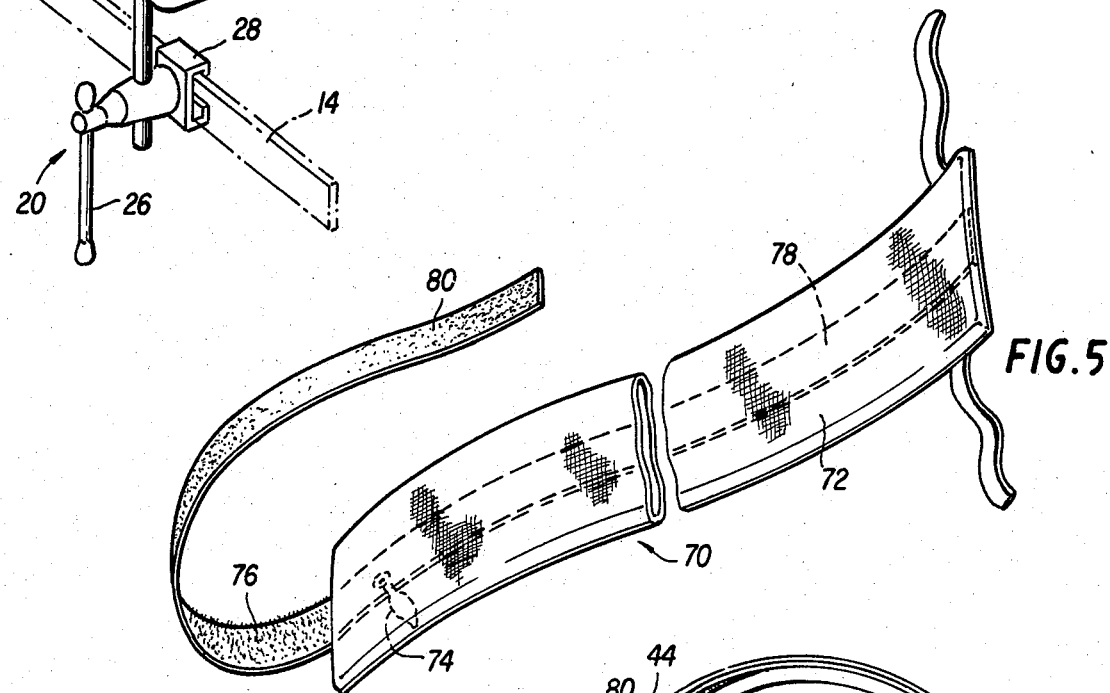
FIG. 5 is a perspective view of a tourniquet used in conjunction with the apparatus of FIG. 1.

As illustrated in FIG. 5, a tourniquet means 70 which constitutes a specially designed sphygmomanometer is provided which includes a main body portion 72 and a valve means shown in phantom at 74 which is attached to the tourniquet means 70 and permits the application of a known amount of pressure to the thigh of the patient. This tourniquet means 70 not only includes Velcro at 76 which is attached to itself on the back side of the main body portion 72 at 78, but also includes Velcro means 80 which is placed exteriorly of the strap and is attached to both the Velcro pad 52 and the Velcro pad 45 attached to strap means 44.

Figure 6:
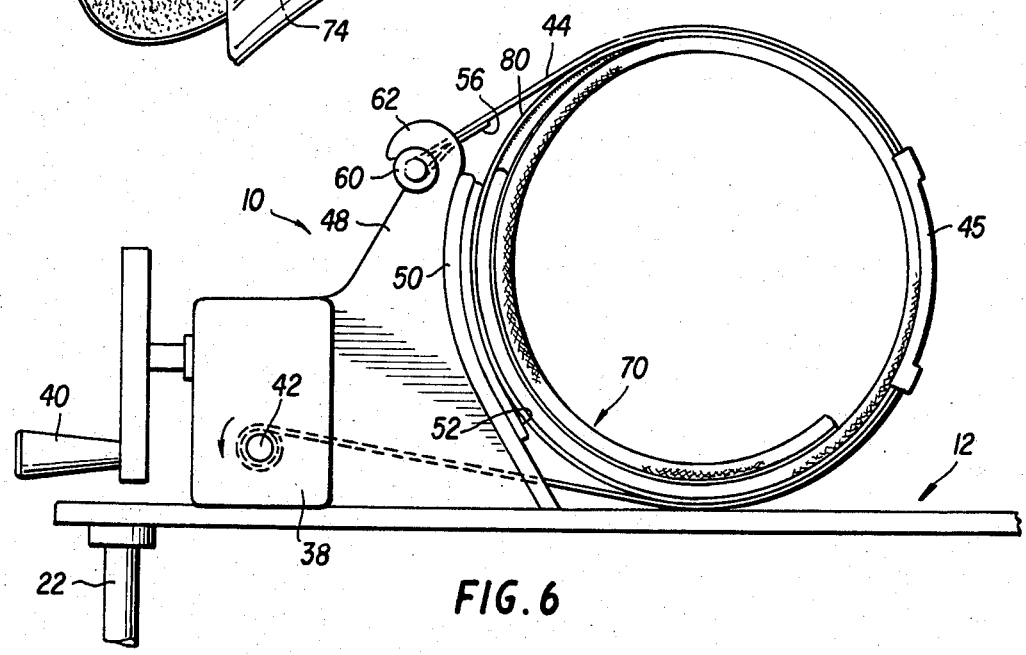
FIG. 6 is a fragmentary elevational view illustrating the position of the tourniquet of FIG. 5 when used with the apparatus of FIG. 1.
Figure 7:
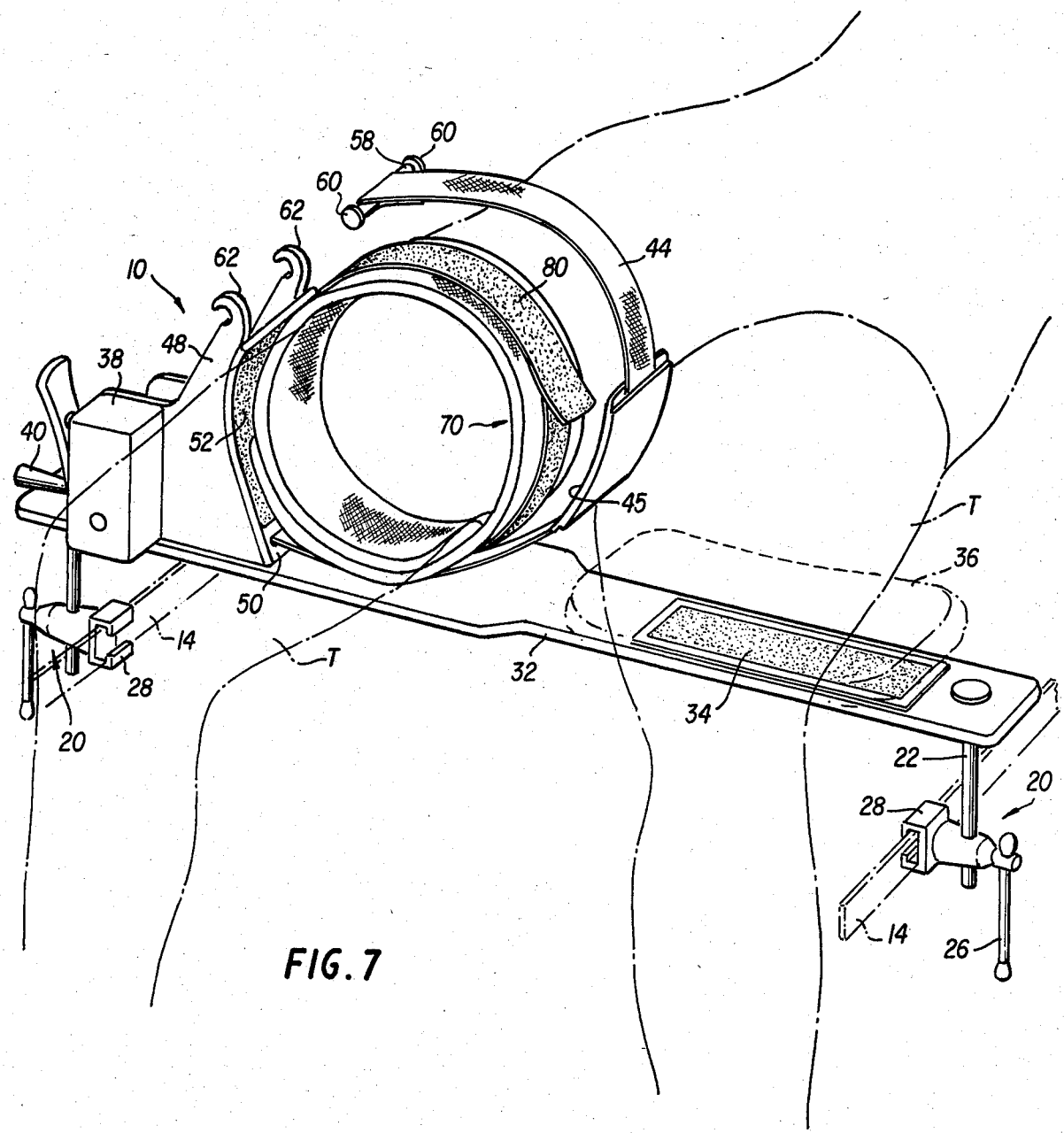
FIG. 7 is a fragmentary perspective view of the apparatus of FIG. 1 and the tourniquet of FIG. 5 used in restraining a thigh of a patient.

In the operation of the embodiment illustrated in FIGS. 1-4, 6 and 7, the thigh restraining apparatus is first clamped to the operating table with the aid of support members 22 which extend into the suitable clamping means provided by the Clark clamps 20. As shown in FIG. 7, the right knee of the patient is in position to be operated upon by restraining the right thigh T of the patient. The left thigh T of the patient is supported by the cushion 36 secured to a Velcro attachment 34 to the narrow portion 32 of bar means 12. The tourniquet means 70 is wrapped around the right thigh T of the patient and the strap 44 is paid out sufficiently far by means of hand crank 40 turning the screw feed means so that the locking rod 58 is manually placed within and retained by the open hook ends 62 in the manner illustrated in FIG. 6. At this time the strap means 44 is tightened by paying in the strap means by turning the crank 40 so that the spool axis 42 turns in a counterclockwise direction as illustrated in FIG. 6 to completely restrain the thigh. The strap 44 is guided laterally or centralized both by the slotted opening at 54 in the curved plate 50 and also by the placement of the end of the strap means 44 between the open hook ends 62 of the mounting plate members 46, 48. The tourniquet 70 is attached on one side of the thigh to the Velcro pad 52 on curved plate 50 and on the other side of the thigh the Velcro pad 45 is secured to the exterior of Velcro portion 80 on the tourniquet 70. It will be observed that the side plate not only fixes the medial side of the thigh to the tourniquet and centralizes the strap over the tourniquet, but also provides a fulcrum for varus stress.

A sterile field is then established over the thighs of the patient in conventional manner, the procedure for which forms no part of this invention. However, the subject invention does allow the leg being operated upon to be removed from the leg holder during surgery without disturbing the sterile field.

The leg holder itself is light weight, being less than 10 lbs. and may be handled and affixed to the operating table by one nurse.

As has already been noted, if the left knee were to be operated upon, the thigh restraining apparatus would be turned end to end and attached to the operating table with the wide portion 30 supporting the thigh restraining apparatus being positioned on the opposite side of the operating table.

In many instances both knees must be operated upon and the apparatus of the present invention envisions the concurrent deployment of a second thigh restraining apparatus designated 10a in FIG. 8 which is a substantial duplication of the thigh restraining apparatus 10 shown in FIGS. 1-4, 6 and 7. Thus, FIG. 8 shows the thigh restraining apparatus 10a attached to the narrow portion 32 of bar means 12 with the aid of suitable attaching means such as the screws 64 illustrated in FIG. 8. In this form of the invention, both legs may be stabilized and restrained simultaneously for bilateral operative cases without disturbing the sterile field. This embodiment of the invention allows transfer of pressure from one thigh to another by independently controlling the screw feed means of the individual thigh restraining means 10, 10a.

While presently preferred embodiments of the invention have been illustrated and described, it will be recognized that the invention may be otherwise variously embodied and practiced within the scope of the claims which follow.

We claim:
1. A thigh restraining apparatus for use in conjunction with an operating table, said operating table having a pair of horizontally extending rail means on opposed sides of said operating table, said apparatus comprising:
 a. bar means extending across said operating table,
 b. means to secure said bar means to said rail means on opposed sides of said operating table, c. tourniquet means applied to the thigh of a patient to be operated upon for stopping the flow of blood in the patient's leg,
d. feed means mounted on said bar means to advance and retard one end of strap means adapted to envelop said tourniquet means,
e. and means for holding said one end of said strap means.

2. A thigh restraining apparatus as defined in claim 1 wherein said strap means carries means for attaching said strap means to said tourniquet means.

3. A thigh restraining apparatus as defined in claim 2 wherein said means carried by said strap means for attaching said strap means to said tourniquet means includes a Velcro member.

4. A thigh restraining apparatus as defined in claim 1 including means for centralizing the feed of said strap means with respect to said tourniquet means.

5. A thigh restraining apparatus as defined in claim 1 including means to vary the lateral spacing between said bar means to secure said bar means to said rail means.

6. A thigh restraining apparatus as defined in claim 1 including feed means mounted on opposite ends of said bar means whereby bilateral operations may be performed on said patient without disturbing a sterile field.

7. A thigh restraining apparatus as defined in claim 4 wherein said means for centralizing the feed of said strap means includes lateral restraining means at two longitudinally spaced locations along said strap means.

8. A thigh restraining apparatus as defined in claim 2 including a plate member fixedly positioned with respect to said bar means, said plate member carrying means for attaching said tourniquet means to said plate member adjacent a location on the patient's thigh substantially opposite from the attachment of said tourniquet means to said strap means.

9. A thigh restraining apparatus as defined in claim 8 wherein said attaching means carried by said plate member is made of Velcro.

10. A method of performing bilateral operations on a patient without disturbing a sterile field, said patient being on an operating table having a pair of horizontally extending rail members on opposite sides of said operating table, said method including the steps of
a. mounting a bar member across said operating table,
b. securing said bar member to said rail members on opposite sides of said operating table,
c. mounting a pair of thigh restraining members on opposite ends of said bar member,
d. holding a tourniquet member around each of the patient's thighs with a respective one of said thigh restraining members,
e. establishing a sterile field over both of the patient's legs,
f. and alternately restraining and releasing the thighs of the patient while performing said bilateral operations without disturbing said sterile field.

* * * * *